United States Patent [19]

Main

[11] 3,957,870

[45] May 18, 1976

[54] ORGANIC COMPOUNDS

[75] Inventor: Brian Geoffrey Main, Macclesfield, England

[73] Assignee: Imperial Chemical Industries Limited, London, England

[22] Filed: Aug. 26, 1975

[21] Appl. No.: 607,932

Related U.S. Application Data

[62] Division of Ser. No. 485,994, July 5, 1974.

[30] Foreign Application Priority Data

July 19, 1973 United Kingdom............... 34465/73

[52] U.S. Cl. .......................... 260/562 N; 260/558 R; 260/559 R; 260/562 A; 260/562 S; 260/562 K
[51] Int. Cl.² ........................................ C07C 103/34
[58] Field of Search ........ 260/559 A, 562 A, 562 B, 260/562 R, 558 A, 558 R, 562 N, 562 S, 562 K

[56] References Cited
UNITED STATES PATENTS

| | | | |
|---|---|---|---|
| 3,644,520 | 2/1972 | Hartley et al. | 260/562 A |
| 3,676,492 | 7/1972 | Biel et al. | 260/562 A |
| 3,712,927 | 1/1973 | Howe et al. | 260/562 A |

*Primary Examiner*—C. Davis
*Attorney, Agent, or Firm*—Cushman, Darby & Cushman

[57] ABSTRACT

Novel 1-hydroxyaryl-2-amidoalkylaminoethanol derivatives, processes for their manufacture, pharmaceutical compositions containing them and methods of using them in the treatment of heart failure and other diseases. The compounds possess β-adrenergic stimulant activity. Representative of the compounds disclosed is 1-p-hydroxyphenyl-2-(β-isobutyramidoethyl)aminoethanol.

6 Claims, No Drawings

ORGANIC COMPOUNDS

This is a division, of application Ser. No. 485,994 filed July 5, 1974.

This invention relates to new phenylethylamine derivatives which possess cardiac or peripheral β-adrenergic stimulant activity.

According to the invention there is provided a new phenylethylamine derivative of the formula:-

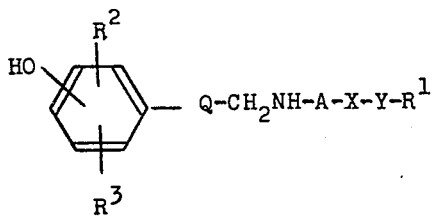

wherein A stands for an alkylene radical of up to 6 carbon atoms, wherein Q stands for the carbonyl (—CO—) or hydroxymethylene (—CHOH—) radical, wherein $R^1$ stands for an alkyl or cycloalkyl radical each of up to 6 carbon atoms, or for an aryl radical of the formula:

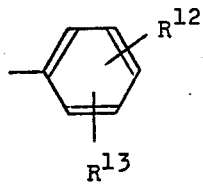

wherein $R^2$, $R^3$, $R^{12}$ and $R^{13}$, which may be the same or different, each stands for a hydrogen or halogen atom, a hydroxy, amino or hydroxymethyl radical, an alkyl, alkoxy, acylamino or alkanesulphonamido radical each of up to 6 carbon atoms, or an aryl radical of up to 12 carbon atoms, wherein X stands for an amidic linkage and wherein Y stands for a direct link, or for an alkylene, alkyleneoxy or iminoalkylenecarbonyloxy radical each of up to 6 carbon atoms, or for the imino (—NH—) radical, or for a radical of the formula —$NR^1$—, wherein $R^1$ has the meaning stated above, or an acid-addition salt thereof.

It will be observed that a phenylethylamine derivative of the invention wherein Q stands for the —CHOH— radical possesses an asymmetric carbon atom, namely the carbon atom of the said —CHOH— group, and it can therefore exist in racemic and optically active forms. It is to be understood that this invention encompasses the racemic form of such a phenylethylamine derivative and any optically active form which possesses β-adrenergic stimulant activity, it being a matter of common general knowledge how a racemic compound may be resolved into its optically-active forms and how the β-adrenergic stimulant activity of these forms may be determined. It is to be understood that β-adrenergic stimulant activity usually predominantes in that optically-active form which has the R absolute configuration of the said —CHOH— group.

A suitable value for the alkylene radical A is, for example, the ethylene, trimethylene, tetramethylene, hexamethylene or 1-methylethylene radical. A is preferably the ethylene or 1-methylethylene radical.

A suitable value for $R^1$ when it stands for an alkyl or cycloalkyl radical is, for example, the methyl, ethyl, n-propyl, isopropyl, n-butyl, isobutyl, t-butyl, cyclopropyl, cyclopentyl or cyclohexyl radical.

A suitable value for $R^2$, $R^3$, $R^{12}$ or $R^{13}$ when it stands for a halogen atom is, for example, the fluorine, chlorine, bromine or iodine atom.

A suitable value for $R^2$, $R^3$, $R^{12}$ or $R^{13}$ when it stands for an alkyl, alkoxy, acylamino or alkanesulphonamido radical is, for example, the methyl, ethyl, n-propyl, methoxy, isopropoxy, acetamido or methanesulphonamido radical.

A suitable value for $R^2$, $R^3$, $R^{12}$ or $R^{13}$ when it stands for an aryl radical is, for example, the phenyl radical.

The amidic linkage X may be a carbonamido radical of the formula —CONH— or —NHCO— or a sulphonamido radical of the formula —$NHSO_2$—.

A suitable value for Y when it stands for an alkylene, alkyleneoxy or iminoalkylenecarbonyloxy radical is, for example, the methylene, ethylene, methyleneoxy, ethyleneoxy, trimethyleneoxy or iminomethylenecarbonyloxy radical. A suitable value for Y when it stands for a radical of the formula —$NR^1$- is, for example, the methylimino radical.

A suitable acid-addition salt of a phenylethylamine derivative of the invention is, for example, a salt derived from an inorganic acid, for example, a hydrochloride, hydrobromide, phosphate or sulphate, or a salt derived from an organic acid, for example, an oxalate, lactate, tartrate, fumarate, acetate, salicylate, citrate, benzoate, β-naphthoate, adipate or 1,1-methylene-bis-(2-hydroxy-3-naphthoate), or a salt derived from an acidic synthetic resin, for example, a sulphonated polystyrene resin.

A preferred phenylethylamine derivative of the invention is a compound of the formula given above wherein A stands for the ethylene or 1-methylethylene radical, wherein Q stands for the hydroxymethylene radical, wherein $R^1$ stands for an alkyl or cycloalkyl radical each of up to 6 carbon atoms or for an unsubstituted phenyl radical, wherein $R^2$ stands for hydrogen or for the hydroxy or methyl radical and $R^3$ stands for hydrogen, wherein X stands for the -NHCO- or —$NHSO_2$- radical and wherein Y stands for the direct link or the imino, methylene or methyleneoxy radical, or an acid-addition salt thereof. A particularly preferred phenylethylamine derivative is such a compound wherein the essential hydroxy radical is in the 4-position of the benzene ring and $R^2$ stands for hydrogen or for a hydroxy radical in the 3-position of the benzene ring, or an acid-addition salt thereof.

Specific phenylethylamine derivatives of the invention are those hereinafter described in the Examples. Of these, preferred compounds by virtue of their high, orally active, cardioselective β-adrenergic stimulant activity are 1-p-hydroxyphenyl-2-(β-isobutyramidoethyl)aminoethanol;

1-p-hydroxyphenyl-2-(β-pivalamidoethyl)aminoethanol;

1-p-hydroxyphenyl-2-(β-phenoxyacetamidoethyl)aminoethanol;

1-p-hydroxyphenyl-2-(β-propionamidoethyl)aminoethanol;

1-m-hydroxyphenyl-2-(β-isobutyramidoethyl)aminoethanol;

1-p-hydroxyphenyl-2-($\beta$-phenylacetamidoethyl-)aminoethanol;

1-p-hydroxyphenyl-2-($\beta$-benzenesulphonamidoethyl)aminoethanol;

1-(3,4-dihydroxyphenyl)-2-($\beta$-isobutyramidoethyl)aminoethanol;

1-(4-hydroxy-3-methylphenyl)-2-($\beta$-isobutyramidoethyl)aminoethanol;

1-p-hydroxyphenyl-2-(1-methyl-2-phenylacetamidoethyl)aminoethanol;

1-p-hydroxyphenyl-2-($\beta$-N-isopropylcarbamoylethyl)aminoethanol;

1-p-hydroxyphenyl-2-($\beta$-3-methoxymethylureidoethyl)aminoethanol;

1-p-hydroxyphenyl-2-($\beta$-3-butoxycarbonylmethylureidoethyl)aminoethanol;

1-(3,4-dihydroxyphenyl)-2-($\beta$-3-phenylureidoethyl)aminoethanol;

1-(4-hydroxy-3-hydroxymethylphenyl)-2-($\beta$-3-phenylureidoethyl)-aminoethanol; and 1-(p-hydroxyphenyl)-2-($\beta$-3-phenylureidoethyl)aminoethanol; and the acid-addition salts thereof.

The phenylethylamine derivative of the invention may be manufactured by any chemical process known to be useful for the manufacture of chemically-analogous compounds.

According to a further feature of the invention there is provided a process for the manufacture of the phenylethylamine derivative of the invention which comprises assembling in sequence, by chemical synthesis, the four radicals;

i. a 2-phenylethyl radical of the formula:-

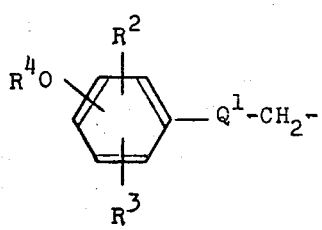

wherein $Q^1$ stands for the carbonyl radical or for a radical of the formula:-

wherein $R^2$ and $R^3$ have the meanings stated above and wherein $R^4$ and $R^5$, which may be the same or different, each stands for hydrogen or for a protecting group;

ii. an imino radical of the formula $-NR^6-$, wherein $R^6$ stands for the hydrogen or for a protecting group;

iii. a radical of the formula $-A-X^1-$ and iv. a radical of the formula $-X^2-Y-R^1$, wherein A, $R^1$ and Y have the meanings stated above and wherein $X^1$ and $X^2$ together form the amidic linkage X, wherein X has the meaning stated above; whereafter if one or more of $R^4$, $R^5$ and $R^6$ stands for a protecting group, the one or more protecting groups are removed.

The various stages of the assembly may be carried out in any possible order. Thus, for example:

a. For the manufacture of a phenylethylamine derivative wherein Q stands for the carbonyl radical, a compound of the formula:-

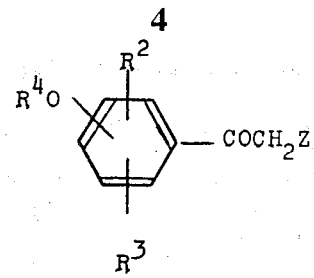

wherein $R^2$, $R^3$ and $R^4$ have the meanings stated above and wherein Z stands for a displaceable radical, may be reacted with an amine of the formula:-

$$HNR^6-A-X-Y-R^1$$

wherein A, $R^1$, $R^6$, X and Y have the meanings stated above, or with a precursor of such an amine.

A suitable value of Z is, for example, a halogen atom, for example the chlorine or bromine atom, or a sulphonyloxy radical, for example, an alkanesulphonyloxy radical of up to 6 carbon atoms or an arenesulphonyloxy radical of up to 10 carbon atoms, for example the methanesulphonyloxy, benzenesulphonyloxy or toluene-p-sulphonyloxy radical.

The reaction may be carried out at ambient temperature and it may be carried out in a diluent or solvent, for example, ethanol, dioxan or acetonitrile. It may also be carried out in the presence of an acid-binding agent, for example, an alkali metal carbonate.

The starting material may be obtained from the corresponding acetophenone derivative either directly by halogenation, when Z stands for a halogen atom, or via the corresponding hydroxy compound of the formula:-

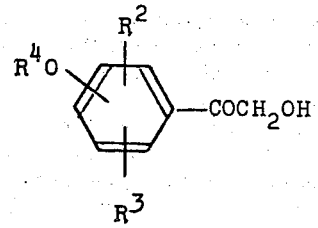

wherein $R^2$, $R^3$ and $R^4$ have the meanings stated above.

b. For the manufacture of a phenylethylamine derivative wherein Q stands for the hydroxymethylene radical, a compound of the formula:-

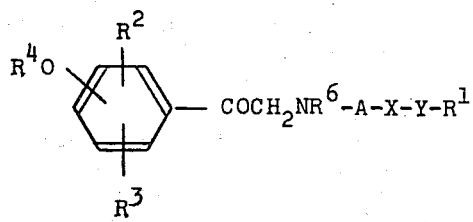

wherein A, $R^1$, $R^2$, $R^3$, $R^4$, $R^6$, X and Y have the meanings stated above, may be reduced.

The reduction may be carried out by means of a metal borohydride, for example, sodium borohydride, in an appropriate diluent or solvent, for example, methanol or ethanol, or by means of catalytic hydrogenation, for example with hydrogen in the presence of a palladium, platinum or nickel catalyst, in a diluent or solvent, for example ethanol or acetic acid.

The starting material may be obtained by the process described under (a) above or under (c) below.

c. A compound of the formula:-

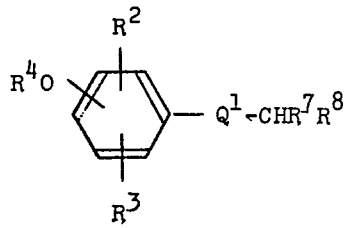

wherein $R^2$, $R^3$, $R^4$ and $Q^1$ have the meanings stated above and wherein either $R^7$ and $R^8$ together form the oxo (=O) radical, or wherein $R^7$ and $R^8$, which may be the same or different, each stands for the hydroxy radical or for an alkoxy radical of up to 6 carbon atoms, may be reacted with an amine of the formula:-

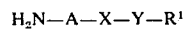

wherein A, $R^1$, X and Y have the meanings stated above, under reducing conditions.

Suitable reducing conditions are provided by, for example, an alkali metal borohydride, for example sodium borohydride, in an appropriate diluent or solvent, for example methanol or ethanol, or by, for example, hydrogen in the presence of a catalyst, for example a platinum, palladium or nickel catalyst, in a diluent or solvent, for example ethanol.

It is to be understood that by varying the reducing conditions a phenylethylamine derivative of the invention wherein Q stands for the carbonyl radical or for the hydroxymethylene radical may be obtained by this process if in the starting material $Q^1$ stands for the carbonyl radical. In particular, if hydrogen and a catalyst are used to provide the reducing conditions, the -CH=N- group in the intermediate product formed, which has the formula:-

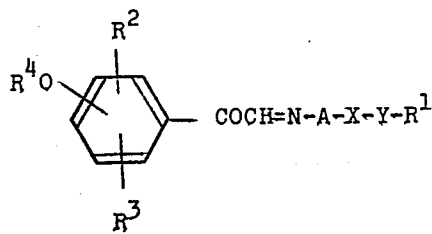

wherein $R^1$, $R^2$, $R^3$, $R^4$, A, X and Y have the meanings stated above, is reduced more readily than the carbonyl group and by stopping the reduction at an appropriate stage a phenylethylamine derivative of the invention wherein Q stands for the carbonyl radical may be obtained. By continuing the reduction a phenylethylamine derivative of the invention wherein Q stands for the hydroxymethylene radical may be obtained.

The starting material wherein $Q^1$ stands for the carbonyl radical may be obtained by the oxidation of an acetophenone derivative of the formula:-

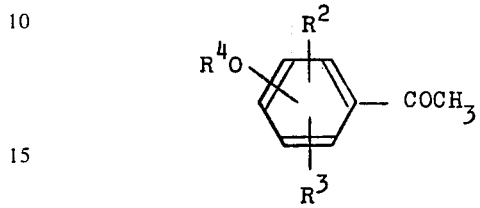

wherein $R^2$, $R^3$, and $R^4$ have the meanings stated above, with selenium dioxide in an appropriate solvent, for example aqueous dioxan, optionally followed by acetal or hemiacetal formation. The starting material wherein $Q^1$ stands for a radical of the formula —CHOH— may be obtained by the reduction of the acetal of the corresponding compound wherein $Q^1$ stands for the carbonyl radical.

d. For the manufacture of a phenylethylamine derivative wherein Q stands for the hydroxymethylene radical, a phenethyl derivative of the formula:-

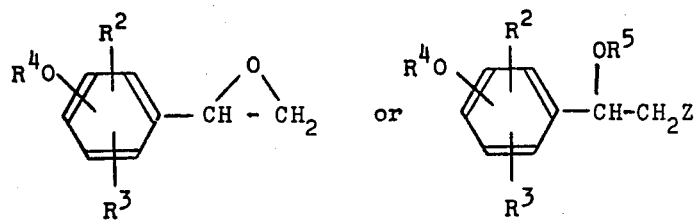

wherein $R^2$, $R^3$, $R^4$, $R^5$ and Z have the meanings stated above, or a mixture of such compounds, may be reacted with an amine of the formula:-

wherein A, $R^1$, $R^6$, X and Y have the meanings stated above, or with a precursor of such an amine.

The reaction may be carried out at ambient temperature or it may be accelerated or completed by the application of heat, for example, by heating to a temperature of 90°–110°C.; it may be carried out at atmospheric or at an elevated pressure, for example by heating in a sealed vessel; and it may be carried out in an inert diluent or solvent, for example methanol, ethanol or isopropanol, or an excess of the amine may be used as diluent or solvent.

Either phenethyl derivative used as starting material, or a mixture thereof, may be obtained by the reduction, for example by means of sodium borohydride or aluminium isopropoxide, of a compound of the formula:-

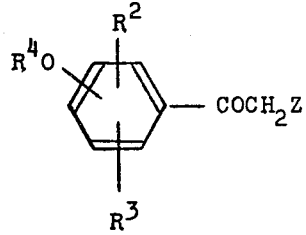

wherein $R^2$, $R^3$, $R^4$ and Z have the meanings stated above.

e. The series of reactions described under (a), (b), (c) or (d) above may be carried out except that an amine of the formula $R^6NH_2$ is used in place of an amine of the formula:-

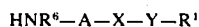

it being understood that when $R^6$ stands for hydrogen the amine is ammonia. The final product obtained, which has the formula:-

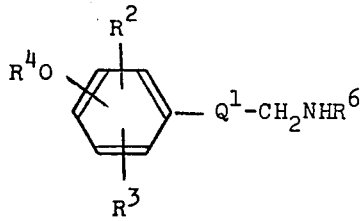

wherein $R^2$, $R^3$, $R^4$, $R^6$ and $Q^1$ have the meanings stated above, may alternatively be obtained, when $R^6$ stands for hydrogen, by the reduction of, for example, a compound of the formula:-

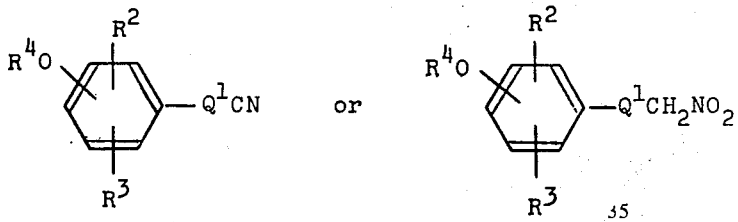

wherein $R^2$, $R^3$, $R^4$ and $Q^1$ have the meanings stated above (which compound may be obtained, when $Q^1$ stands for the —CHOH— radical, by the reaction of the corresponding benzaldehyde derivative with, respectively, hydrogen cyanide or nitromethane), or by the reduction of an oxime of the formula:-

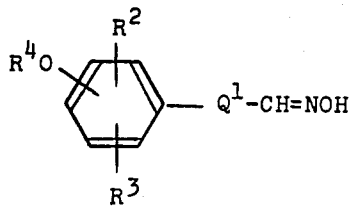

wherein $R^2$, $R^3$, $R^4$ and $Q^1$ have the meanings stated above (which oxime may be obtained by conventional means from the corresponding aldehyde), or by the reduction of any other suitable compound which contains a group reducible to a primary amino group, for example, a diazo or azido group.

The radical —A—X—Y—$R^1$ may then be inserted as a separate step, for example either by the reaction of the final product from the series of reactions described under (a), (b), (c) or (d) above with a compound of the formula:-

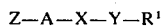

wherein A, $R^1$, X, Y and Z have the meanings stated above, or, when $R^6$ stands for hydrogen, by the reaction under reducing conditions of the final product from the series of reactions described under (a), (b), (c) or (d) above with a carbonyl compound of the formula:-

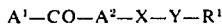

wherein $R^1$, X and Y have the meanings stated above and wherein $A^1$ stands for hydrogen or for an alkyl radical and $A^2$ stands for an alkylene radical such that the radical

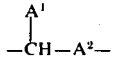

has the same meaning as is stated above for A.

The reaction involving a compound of the formula:-

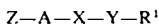

may conveniently be carried out in the presence of a base, for example sodium or potassium carbonate, in a diluent or solvent, for example ethanol or isopropanol, at an elevated temperature, for example at the boiling point of the diluent or solvent.

Suitable reducing conditions for the reaction involving the carbonyl compound are those provided by the presence of hydrogen and a hydrogenation catalyst, for example palladium or platinum, in an inert diluent or solvent, for example in one or more solvents selected from water and ethanol; or by the presence of an alkai metal borohydride, for example sodium borohydride or lithium cyanoborohydride, in an inert diluent or solvent, for example in one or more solvents selected from water, ethanol and methanol.

f. The series of reactions described under (a), (b), (c), (d) or (e) above may be carried out except that an amine containing a radical of the formula:-

wherein A, $R^6$ and $X^1$ have the meanings stated above, is used in place of a amine of the formula:-

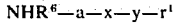

or the reaction described under (e) above may be carried out except that the radical —A—$X^1$— is inserted in place of the radical —A—X—Y—$R^1$. The amidic linkage X may then be formed as a separate step by insertion of a radical of the formula —$X^2$—Y—$R^1$, wherein $R^1$, $X^2$ and Y have the meanings stated above.

$X^1$ may be, for example, an imino radical of the formula —$NR^6$—, wherein $R^6$ has the meaning stated above, in which case $X^2$ may be the carbonyl (—CO—) or sulphonyl (—$SO_2$—) radical. Alternatively, $X^1$ may be the carbonyl or sulphonyl radical, in which case $X^2$ may be the imino radical. When $X^1$ is an imino radical, an amine containing the radical of the formula $HNR^6$—A—$X^1$ may be, for example, an amine of the formula $HNR^6$—A—$NHR^6$, wherein $R^6$, the two values of which may be the same or different, and A have the meanings stated above, and the radical of the formula —$X^2$—Y—$R^1$ may be inserted by reaction with a compound of the formula $Z^1$CO—Y—$R^1$ or $Z^1SO_2$—Y—$R^1$, wherein $R^1$ and Y have the meanings stated above and wherein $Z^1$ stands for a displaceable radical, for example a halogen atom or a lower alkoxy radical, or with an anhydride of the formula $(R^1-Y-CO)_2O$,, or, when Y stands for the imino radical, with an isocyanate of the formula $R^1$NCO.

When $X^1$ is the carbonyl or sulphonyl radical an amine containing the radical of the formula $HNR^6$—A—$X^1$ may be, for example, an amine of the formula $HNR^6$—A—$COZ^2$, wherein A and $R^6$ have the meanings stated above and wherein $Z^2$ stands for a displaceable radical or for a radical capable of being converted into a displaceable radical. The radical of the formula —$X^2$—Y—$R^1$ may then be inserted by reaction with a compound of the formula $HNR^6$—Y—$R^1$, wherein $R^1$, $R^6$ and Y have the meanings stated above.

When $Z^2$ stands for a displaceable radical this radical must be such that the compound of the formula $HNR^6$—A—$COZ^2$ is relatively stable. $Z^2$ may be, for example, an alkoxy radical of up to 6 carbon atoms, for example the methoxy or ethoxy radical. If a more reactive displaceable radical is desired, $Z^2$ must be a relatively inert radical such as the hydroxy radical or an alkoxy radical which may be converted into a reactive displaceable radical such as a radical of the formula —$Z^1$, wherein $Z^1$ has the meaning stated above, for example the chloro radical.

The starting material for the last mentioned reaction, which is a compound containing the radical

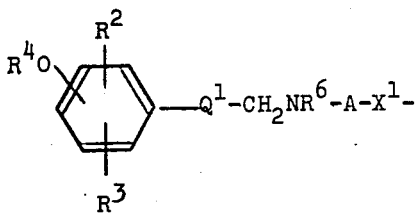

wherein $R^2$, $R^3$, $R^4$, $R^6$, A, $Q^1$ and $X^1$ have the meanings stated above, may alternatively be obtained by the hydrolysis, for example with an alcoholic alkali metal hydroxide solution, of the amide linkage X in a compound of the formula:

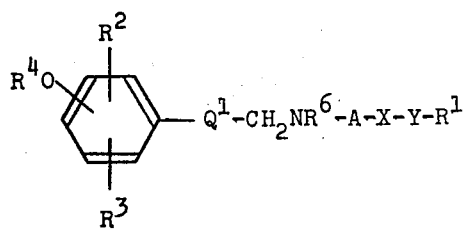

wherein $R^1$, $R^2$, $R^3$, $R^4$, $R^6$, A, $Q^1$, X and Y have the meanings stated above, which may be obtained as described under (a), (b), (c), (d), or (e) above. g. A compound wherein one or more of $R^4$, $R^5$ and $R^6$ stands for a protecting group may be prepared by the series of reactions described under (a), (b), (c), (d), (e) or (f) above. Alternatively, a suitable protecting group may be introduced by conventional means into an intermediate compound at any stage preceding the final stage.

A suitable value for $R^4$ or $R^5$ when it stands for a protecting group is, for example, a hydrogenolysable radical, for example an α-arylalkyl, α-arylalkoxy-carbonyl or α-arylalkoxymethyl radical, for example the benzyl, benzyloxycarbonyl or benzyloxymethyl radical, or an acyl radical, for example an alkanoyl radical of up to 20 carbon atoms, for example the acetyl, t-butoxycarbonyl or 2,2,2-trichloroethoxycarbonyl radical, or an aroyl radical of up to 10 carbon atoms, for example the benzoyl radical, or an α-alkoxyalkyl radical (that is, a radical which forms with the adjacent oxygen atom an acetal radical), for example the tetrahydropyranyl radical, or a tertiary alkyl radical, for example the t-butyl radical.

A suitable value for $R^6$ when its stands for a protecting group is, for example, a hydrogenolysable or tertiary alkyl radical as defined for $R^4$ or $R^5$, or a relatively easily hydrolysable acyl radical, for example the 2,2,2-trichloroethoxycarbonyl or t-butoxycarbonyl radical. It is to be understood that when $Rk^6$ stands for an acyl radical, this radical must be removable under conditions which will not destroy the amidic linkage X.

Alternatively, $R^5$ and $R^6$ may be joined together so that one protecting group serves to protect both the oxygen and nitrogen atoms. Such protecting group may be, for example, a radical of the formula —$CHR^9$—, wherein $R^9$ stands for hydrogen, or for an alkyl radical of up to 4 carbon atoms or an aryl radical of up to 10 carbon atoms, such that it forms, together with the adjacent oxygen and nitrogen atoms and the two adjacent carbon atoms, an oxazolidine nucleus.

The hydrogenolysable protecting group $R^4$, $R^5$ or $R^6$ may be removed, for example, by catalytic hydrogenation, for example by hydrogenation in the presence of a palladium-on-charcoal catalyst, in an inert diluent or solvent, for example ethanol, aqueous ethanol or acetic acid. The process may be accelerated or completed by the presence of an acidic catalyst, for example hydrochloric or oxalic acid.

The acyl protecting group $R^4$, $R^5$ or $R^6$ may be removed by hydrolysis in the presence of a base, for example an alkali metal hydroxide, in a diluent or solvent, for example water, methanol, ethanol or a mixture thereof. It is to be understood that the hydrolytic conditions used must be sufficiently mild to avoid hydrolysis of the amidic linkage X.

The α-alkoxyalkyl protecting group $R^4$ or $R^5$ or the protecting group —$R^9$CH—formed by $R^5$ and $R^6$ taken together may be removed by hydrolysis in the presence of an acid, for example a mineral acid, for example aqueous hydrochloric acid, and the hydrolysis may be carried out at a moderate temperature such that the amidic linkage X is not also hydrolysed.

The tertiary alkyl protecting group $R^4$, $R^5$ or $R^6$ or the acyl protecting group $R^4$, $Rk^5$ or $R^6$ when it stands for a tertiary alkoxycarbonyl radical, for example the t-butoxycarbonyl radical, may be removed by treatment with an acid, for example hydrogen chloride, in anhydrous conditions, for example in ethereal solution.

One preferred process for the manufacture of a preferred phenylethylamine derivative of the invention wherein Q stands for the hydroxymethylene radical comprises the reaction of a compound of the formula:

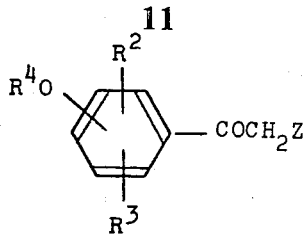

wherein $R^2$ and $R^3$ have the meanings stated above, wherein $R^4$ stands for hydrogen or the benzyl radical and wherein Z stands for a halogen atom, preferably the bromine atom, with an amine of the formula:-

wherein A, $R^1$, X and Y have the meanings stated above and whererin $R^6$ stands for hydrogen or for the benzyl radical, followed by the reduction of the carbonyl radical with an alkali metal borohydride or by catalytic hydrogenation, and either the simultaneous or subsequent conversion by catalytic hydrogenolysis of a compound wherein, if appropriate, $R^4$ and/or $R^6$ stands for the benzyl radical to the corresponding compound wherein $R^4$ and $R^6$ both stand for hydrogen. In this process preferably $R^4$ and $R^6$ in the starting material both stand for the benzyl radical.

A second preferred process for the manufacture of a preferred phenylethylamine derivative of the invention wherein Q stands for the hydroxymethylene radical comprises the reaction of a compound of the formula:-

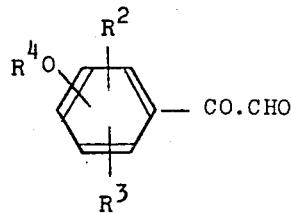

wherein $R^2$ and $R^3$ have the meanings stated above and wherein $R^4$ stands for hydrogen or the benzyl radical, or a hydrate thereof, with an amine of the formula:-

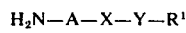

wherein A, $R^1$, X and Y have the meanings stated above, in the presence of hydrogen and a hydrogenation catalyst.

A third preferred process for the manufacture of a preferred phenylalkylamine derivative of the invention wherein Q stands for the hydroxymethylene radical and X stands for the —NHCO— or —NHSO$_2$— radical comprises the reaction of a compound of the formula:-

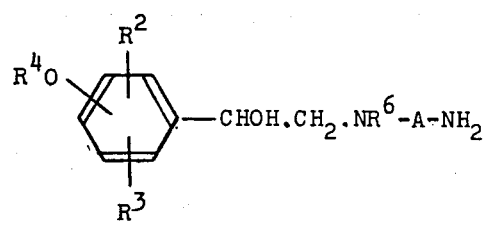

wherein $R^2$, $R^3$ and A have the meanings stated above and wherein $R^4$ and $R^6$ both stand for protecting groups, preferably both being benzyl radicals, with a compound of the formula:-

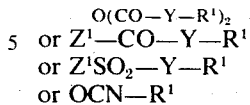

wherein $R^1$, Y and $Z^1$ have the meanings stated above, whereafter both protecting groups $R^4$ and $R^6$ are removed, preferably if both are benzyl radicals by catalytic hydrogenolysis.

Optically-active forms of a phenylethylamine derivative of the invention wherein Q stands for the hydroxymethylene radical may be obtained by the resolution by conventional means of the corresponding racemic phenylethylamine derivative of the invention.

The said resolution may be carried out by reacting the racemic phenylethylamine derivative with an optically-active acid, followed by fractional crystallisation of the diastereoisomeric mixture of salts thus obtained from a diluent or solvent, for example, ethanol, whereafter the optically-active phenylethylamine derivative is liberated from the salt by treatment with a base. A suitable optically-active acid is, for example, (+)— or (−)—O, O—di-p-toluoyltartaric acid.

The resolution process may be facilitated by treating the partially resolved phenylethylamine derivative in free base form obtained after a single fractional crystallisation of the diastereoisomeric mixture of salts with a solubilising agent, for example a primary amine, for example, allylamine, in a relatively non-polar diluent or solvent, for example petroleum ether.

The phenylethylamine derivative of the invention in free base form may be converted into an acid-addition salt thereof by reaction with an acid by conventional means.

As stated above, the phenylethylamine derivative of the invention or an acid-addition salt thereof possesses cardiac or peripheral β-adrenergic stimulant activity. This may be demonstrated in either conscious or pentobarbitoneanaesthetised dogs, where a cardiac β-stimulant phenylethylamine derivative or salt thereof produces an increase in heart rate, an increase in force of contraction of the heart and an increase in the speed of conduction of electrical activity through the tissues of the heart, or where a peripheral β-stimulant phenylethylamine derivative produces a fall in blood pressure. These effects are prevented by the administration of a β-adrenergic blocking agent such as propranolol. Unlike isoprenaline, a known β-adrenergic stimulating agent, a phenylethylamine derivative of the invention or a salt thereof is well absorbed when administered orally and has a substantial duration of action. At doses of a phenylethylamine derivative of the invention which produce effective β-adrenergic stimulation in dogs, no symptoms of toxicity are apparent.

Many of the phenylethylamine derivatives of the invention possess, in addition to β-adrenergic stimulant activity, considerable β-adrenergic blocking activity as measured by the inhibition of isoprenaline-induced tachycardia in rats or cats.

The phenylethylamine derivative of the invention may be administered to warm-blooded animals, including man, in the form of a pharmaceutical composition comprising as active ingredient at least one phenylethylamine derivative of the invention, or an acid-addition salt thereof, in association with a pharmaceutically acceptable diluent or carrier therefor.

A suitable composition is, for example, a tablet, capsule, aqueous or oily solution or suspension, emulsion, injectable aqueous or oily solution or suspension, dispersible powder, spray or aerosol formulation.

The pharmaceutical composition may contain, in addition to the phenylethylamine derivative of the invention, one or more drugs selected from sedatives, for example phenobarbitone, meprobamate, chlorpromazine and the benzodiazepine sedative drugs, for example chlordiazepoxide and diazepam; vasodilators, for example glyceryl trinitrate, pentaerythritol tetranitrate and isosorbide dinitrate; diuretics, for example chlorothiazide; hypotensive agents, for example reserpine, bethanidine and guanethidine; cardiac membrane stablilising agents, for example quinidine; agents used in the treatment of Parkinson's disease and other tremors, for example benzhexol; cardiotonic agents, for example digitalis preparations; α-adrenergic blocking agents, for example phentolamine; and sympathomimetic bronchodilators, for example isoprenaline, orciprenaline, adrenaline and ephedrine.

When used for the treatment of acute or chronic heart failure, or hypertension or bronchospasm in man, it is expected that the phenylethylamine derivative would be given to man at a total oral or intravenous dose of between 1 mg. and 100 mg. daily, preferably between 1 mg. and 10 mg. daily, at doses spaced at 6–8 hourly intervals. Preferred oral dosage forms are tablets or capsules containing between 1 and 10 mg. and preferably 1 mg. or 5 mg. of active ingredient. Preferred intravenous dosage forms are sterile aqueous solutions of the phenylethylamine derivative or of a non-toxic acid-addition salt thereof, containing between 0.05 percent and 1 percent w/v of active ingredient, and more particularly containing 0.1 percent w/v of active ingredient.

The invention is illustrated but not limited by the following Examples:-

EXAMPLE 1

A mixture of 1.30 g. of N-(β-aminoethyl)isobutyramide, 20 ml. of ethanol and 0.5 g. of a 30 percent palladium-on-charcoal catalyst is stirred at laboratory temperature under an atmosphere of hydrogen, and a solution of 1.68 g. of p-hydroxyphenylglyoxal in 15 ml. of ethanol is added dropwise during 50 minutes. Hydrogen (220 ml.) is rapidly absorbed during this time, and the mixture is stirred for a further 40 hours during which time a further 275 ml. of hydrogen are absorbed. The mixture is filtered, the filtrate is evaporated to dryness under reduced pressure and the residue is dissolved in a mixture of ethanol and ethyl acetate. An excess of ethereal oxalic acid solution is added, and the mixture is filtered. The solid residue is crystallised from water and there is thus obtained 1-p-hydroxyphenyl-2-(β-isobutyramidoethyl)aminoethanol hydrogen oxalate, m.p. 215°–216°C.

The process described above is repeated except that an equivalent amount of N-(β-aminoethyl)pivalamide or N-(β-aminoethyl)phenoxyacetamide is used as starting material in place of N-(β-aminoethyl)isobutyramide, and that in the former case the product is isolated as free base. There are thus obtained respectively 1-p-hydroxyphenyl-2-(β-pivalamidoethylamino)-ethanol, m.p. 144°C. and 1-p-hydroxyphenyl-2-(β-phenoxyacetamidoethyl)aminoethanol hydrogen oxalate hemihydrate, m.p. 185.5°–186.5°C.

EXAMPLE 2

The process described in Example 1 is repeated except that an equivalent amount of 1-β-aminoethyl-3-phenylurea or p-acetamido-N-(β-aminoethyl)benzamide is used as starting material, that the hydrogenation is interrupted after the addition of amide is complete and acetic acid is added to dissolve the precipitated p-hydroxyacetophenone derivative formed as intermediate, a further 0.5 g. of catalyst also being added, and that in the latter case the product is isolated as an acetate instead of an oxalate. There is thus obtained respectively 1-p-hydroxyphenyl-2-(β-3-phenylureido-ethyl)amino ethanol hydrogen oxalate hemihydrate, m.p. 160°–162°C., and 2-β-(p-acetamidobenzamido)ethylamino-1-p-hydroxyphenylethanol acetate, m.p. 175°–176°C.

EXAMPLE 3

A mixture of 1.32 g. of N-(β-aminoethyl)-2-methoxyacetamide, 20 ml. of ethanol and 0.5 g. of a 30 percent palladium-on-charcoal catalyst is stirred at laboratory temperature under an atmosphere of hydrogen, and a solution of 1.68 g. of p-hydroxyphenylglyoxal in 15 ml. of ethanol is added dropwise during 50 minutes. The mixture is stirred until rapid absorption of hydrogen ceases, and is then filtered. The filtrate is evaporated to dryness under reduced pressure, the residue is dissolved in methanol and an ethereal solution of oxalic acid is added. The mixture is filtered and the solid product is crystallised from water. There is thus obtained N-β-(2-p-hydroxyphenyl-2-oxoethylamino)ethyl-2-methoxyacetamide hydrogen oxalate hemihydrate, m.p. 199°–200°C. with decomposition.

The process described above is repeated except that N-(β-aminoethyl)benzamide or N-(β-aminoethyl)benzenesulphonamide is used as starting material in place of N-(β-aminoethyl)-2-methoxyacetamide. There are thus obtained respectively N-β-(2-p-hydroxyphenyl-2-oxoethylamino)ethylbenzamide oxalate, m.p. 225°–227°C. (with decomposition) after crystallisation from ethanol, and N-β-(2-p-hydroxyphenyl-2-oxoethylamino)ethylbenzenesulphonamide oxalate, m.p. 176°–179°C. (with decomposition) after crystallisation from water.

EXAMPLE 4

A mixture of p-benzyloxyphenacyl bromide (12.2 g.), N-benzyl-N-β-isobutyramidoethylamine hydrochloride (10.28 g.), anhydrous potassium carbonate (13.8 g.) and ethanol (200 ml.) is stirred at laboratory temperature for 16 hours. An excess of sodium borohydride (approximately 4.0 g.) is then added and the mixture is stirred for a further 1 hour and then diluted with 300 ml. of water and extracted with ethyl acetate. The extract is dried and evaporated to dryness and there is thus obtained as solid residue 1-p-benzyloxyphenyl-2-(N-benzyl-N-β-isobutyramidoethylamino)ethanol. A solution of this compound in a mixture of 25 ml. of ethanol and 75 ml. of acetic acid is shaken with hydrogen and a 30 percent palladium-on-charcoal catalyst at atmospheric pressure and laboratory temperature until uptake of hydrogen ceases. The mixture is filtered, the filtrate is evaporated to dryness and the residue is dissolved in ethanol. An excess of a solution of oxalic acid in ether is added, the mixture is filtered and the solid product is crystallised from water. There is thus obtained 1-p-hydroxyphenyl-2-(β- isobutyramidoethylamino)ethanol hydrogen oxalate, m.p. 215°–216°C.

The process described above is repeated except that the appropriate N-benzyl-N-β-amidoethylamine is used as starting material in place of N-benzyl-N-β-isobutyramidoethylamine. There are thus obtained the compounds shown in the following table:- spectively 1-(3,4-dihydroxyphenyl)-2-(β-isobutyramidoethyl)aminoethanol, characterised either as the oxalate, m.p. 150°–151°C. (with decomposition) or the hydrogen oxalate hemihydrate, m.p. 175°C. (with decomposition), and 1-o-hydroxyphenyl-2-(β-isobutyramidoethyl)aminoethanol oxalate hemihydrate, m.p. 74°–76°C., all three salts being crystal-

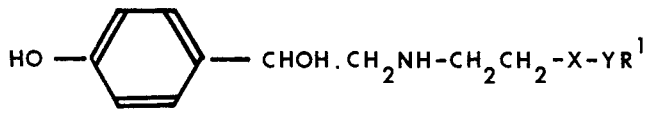

| X | YR¹ | salt | m.p.°C. | crystallisation solvent |
| --- | --- | --- | --- | --- |
| —NHCO— | p-methoxybenzyl | oxalate | 103–105 | ethanol/ether |
| —NHSO₂— | phenyl | oxalate | 139–140(d) | ethanol |
| —CONH— | isopropyl | oxalate hydrate | 49–50 | isopropanol |
| —CONH— | p-acetamidophenyl | oxalate | 173 | water |
| —CONH— | β-phenylethyl | oxalate | 99–101 | isopropanol |

The process described above is repeated except that 3,4-dibenzyloxyphenacyl bromide and N-benzyl-N-(β-3-phenylureidoethyl)amine are used as starting materials. There is thus obtained 1-(3,4-dihydroxyphenyl)-2-(β-3-phenylureidoethyl)aminoethanol oxalate, m.p. 98°–100°C. (with decomposition) after crystallisation from acetonitrile.

EXAMPLE 5

A mixture of m-benzyloxyphenacyl bromide (7.0 g.) N-benzyl-N-β-isobutyramidoethylamine (8.8 g.) and dioxan (150 ml.) is stirred at laboratory temperature for 16 hours and then evaporated to dryness under reduced pressure. The residue is shaken with a mixture of water and ethyl acetate and the ethyl acetate solution is separated, washed with water, dried and evaporated to dryness. The residue is dissolved in 200 ml. of ethanol, an excess of sodium borohydride (approximately 3.0 g.) is added and the mixture is stirred at laboratory temperature for 1 hour, diluted with 300 ml. of water and extracted with ethyl acetate. The ethyl acetate solution is washed with water, dried and evaporated to dryness and the residual oil is dissolved in a mixture of 25 ml. of ethanol and 75 ml. of acetic acid. The solution is shaken with hydrogen and a 30 percent palladium-on-charcoal catalyst at atmospheric pressure and laboratory temperature until uptake of hydrogen is complete. The mixture is filtered, the filtrate is evaporated to dryness and the residue is dissolved in ethanol. An excess of a solution of oxalic acid in ether is added, the mixture is filtered and the solid product is crystallised from a mixture of ether and ethanol. There is thus obtained 1-m-hydroxyphenyl-2-(β-isobutyramidoethyl)aminoethanol hydrogen oxalate hemihydrate, m.p. 164°–166°C. (with decomposition).

The process described above is repeated except that either 3,4-dibenzyloxyphenacyl bromide or o-benzyloxyphenacyl bromide is used in place of m-benzyloxyphenacyl bromide. There are thus obtained re- lised from ethanol.

The process described above is repeated except that N-benzyl-N-(β-3-phenylureidoethyl)amine is used as starting material in place of N-benzyl-N-β-isobutyramidoethylamine. There is thus obtained 1-m-hydroxyphenyl-2-(β-3-phenylureidoethyl)aminoethanol oxalate hemihydrate, m.p. 111°–112°C. after crystallisation from a mixture of ethanol and ether.

The o-benzyloxyphenacyl bromide used as starting material may be obtained as follows:-

A stirred mixture of o-hydroxyacetophenone (136 g.), benzyl chloride (172 ml.), anhydrous potassium carbonate (276 g.) and ethanol (1 liter) is heated under reflux for 65 hours, cooled, diluted with water and extracted with ethyl acetate. The extract is washed with water, dried and evaporated to dryness. A solution of the crude residual o-benzyloxyacetophenone (49.7 g.) in chloroform (160 ml.) is added to a stirred suspension of cupric bromide (89.2 g.) in ethyl acetate (160 ml.) which is heated under reflux, and heating is continued until the green colour of the cupric bromide is discharged. The mixture is cooled and filtered and the filtrate is shaken with a mixture of toluene, ether and water. The organic layer is separated, washed with water, dried and evaporated to dryness and the residual oil (30 g.) is chromatographed on a column of 400 g. of silica gel (Hopkin & Williams M.F.C., 100-200 mesh) using chloroform as eluant. The eluate is evaporated to dryness and there is thus obtained as residue o-benzyloxyphenacyl bromide, which is a low-melting solid used without further purification.

EXAMPLE 6

The process described in Example 5 is repeated using the appropriate benzyloxyphenacyl bromide and the appropriate N-benzyl-N-β-amidoethylamine as starting materials, and also using acetonitrile in place of dioxan as solvent. There are thus obtained the compounds described in the following table:-

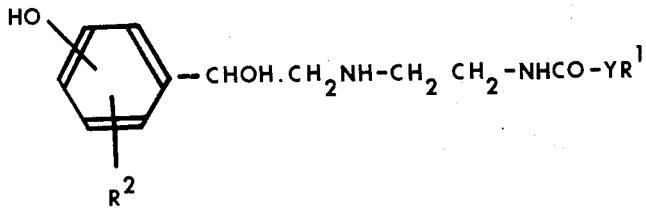

| Position of HO | R² | Y¹R | salt | m.p.°C. | crystallisation solvent |
|---|---|---|---|---|---|
| 3- | 5-hydroxy | anilino | hydrogen oxalate hemihydrate | 203–205 | methanol |
| 3- | 5-hydroxy | isopropyl | oxalate hydrate | 118–120 | (wash with ether) |
| 4- | 3-methyl | isopropyl | hydrogen oxalate | 176 | ethanol |
| 4- | 3-methyl | anilino | hydrogen oxalate hemihydrate | 150–153 | ethanol |

The 4-benzyloxy-3-methylphenacyl bromide used as starting material may be obtained as follows:-

A stirred mixture of 4-hydroxy-3-methylacetophenone (50 g.), benzyl chloride (52.7 g.), anhydrous potassium carbonate (57.5 g.) and acetone (400 ml.) is heated under reflux for 72 hours and then poured into 1 litre of water. The mixture is extracted three times with ethyl acetate and the extract is washed successively with aqueous 2N-sodium hydroxide solution (twice) and water, dried and evaporated to dryness.

A solution of the 4-benzyloxy-3-methylacetophenone (64 g.) thus obtained in hot chloroform (250 ml.) is added to a stirred suspension of cupric bromide (99 g.) in ethyl acetate (250 ml.) which is heated under reflux in a current of nitrogen, and the mixture is stirred and heated under reflux until the green colour of the cupric bromide is discharged. The mixture is cooled and filtered, the filtrate is evaporated to dryness and the residue is partitioned between ethyl acetate and aqueous 2N-sodium hydroxide solution. The organic phase is separated, washed with water, dried over magnesium sulphate and evaporated to dryness, and the residual purple solid is crystallised from ethanol. There is thus obtained 4-benzyloxy-3-methylphenyacyl bromide, m.p. 100°–102°C.

EXAMPLE 7

A mixture of 4-benzyloxy-3-methanesulphonamidophenacyl bromide (3.98 g.), N-benzyl-N-β-isobutyramidoethylamine (4.36 g.) and acetonitrile (25 ml.) is stirred at laboratory temperature for 30 minutes, diluted with 150 ml. of ether and filtered. The filtrate is evaporated to dryness and the solid residue, which is the salt of N-benzyl-N-β-isobutyramidoethylamine with N-β-[N-benzyl-N-(2-4'-benzyloxy-3'-methanesulphonamidophenyl-2-oxoethyl)amino]ethylisobutyramide, is shaken with a mixture of 100 ml. of aqueous 2N-hydrochloric acid and 100 ml. of ethyl acetate. The mixture is filtered and the solid residue is washed with water and with ethyl acetate and dissolved in 50 ml. acetic acid. The solution is shaken with hydrogen and a 30 percent palladium-on-charcoal catalyst at atmospheric pressure and laboratory temperature until uptake of hydrogen ceases. The mixture is filtered and an excess of a solution of oxalic acid in ether is added to the filtrate. The mixture is filtered and the solid residue is crystallised from a mixture of methanol and ether. There is thus obtained 1-(4-hydroxy-3-methanesulphonamidophenyl)- 2-(β-isobutyramidoethyl)aminoethanol oxalate hydrate, m.p. 213°–215°C.

The process described above is repeated except that N-benzyl-N-(β-3-phenylureidoethyl)amine is used as starting material in place of N-benzyl-N-β-isobutyramidoethylamine. There is thus obtained 1-(4-hydroxy-3-methanesulphonamidophenyl)-2-(β-3-phenylureidoethyl)aminoethanol oxalate hydrate, m.p. 120°C after crystallisation from a mixture of ethanol and ether.

EXAMPLE 8

A mixture of 1-(4-benzyloxy-3-ethoxycarbonylphenyl)-2-bromoethanol (11.3 g.), N-benzyl-N-(β-3-phenylureidoethyl)-amine hydrochloride (9.15 g.) aqueous 2N-sodium hydroxide solution (30 ml.) and isopropanol (100 ml.) is heated under reflux for 16 hours, diluted with water and extracted with ethyl acetate. The extract is washed with water, dried and evaporated to dryness and the residue is dissolved in a small volume of ethanol. An excess of a solution of oxalic acid in ether is added, the mixture is rapidly filtered, the solid being discarded, and the filtrate is allowed to stand, when crystallisation slowly takes place. The mixture is filtered and there is thus obtained as solid residue 1-(4-benzyloxy-3-ethoxycarbonylphenyl)-2-N-benzyl-N-(β-3-phenylureidoethyl)-aminoethanol oxalate.

Sodium borohydride (8.3 g.) is slowly added to a stirred solution of the above compound (4.7 g.) in a mixture of 15 ml. of tetrahydrofuran and 7 ml. of methanol and the mixture is stirred for 4 hours at laboratory temperature. Further sodium borohydride (5 g.) is added and the mixture is stirred for a further 8 days and then diluted with water and extracted with ethyl acetate. The extract is washed with water, dried and evaporated to dryness and the residue is dissolved in acetic acid and shaken with hydrogen and a 30 percent palladium-on-charcoal catalyst at atmospheric pressure and laboratory temperature until uptake of hydrogen ceases. The mixture is filtered and the filtrate is evaporated to dryness under reduced pressure. The residue is dissolved in ethanol, an excess of a solution of oxalic acid in ether is added and the mixture is filtered. The solid product is crystallised from a mixture of ethanol and ether and there is thus obtained 1-(4-hydroxy-3-hydroxymethylphenyl)-2-($\beta$-3-phenylureidoethyl)-aminoethanol oxalate, m.p. 132°–134°C.

EXAMPLE 9

The process described in Example 5 is repeated except that 4-benzyloxy-3-ethoxycarbonylphenacyl bromide is used as starting material in place of m-benzyloxyphenacyl bromide, and that the hydrogenation step is not carried out. There is thus obtained crude 1-(4-benzyloxy-3-ethoxycarbonylphenyl)-2-(N-benzyl-N-$\beta$-isobutyramidoethylamino)ethanol. This compound is treated with sodium borohydride and methanol in tetrahydrofuran by a similar process to that described in Example 8, and the intermediate product thus obtained is treated with hydrogen and a 30 percent palladium-on-charcoal catalyst also as described in Example 8. There is thus obtained 1-(4-hydroxy-3-hydroxymethylphenyl)-2-($\beta$-isobutyramidoethyl)-aminoethanol hydrogen oxalate hemihydrate, m.p. 176°–178°C. (with decomposition) after crystallisation from a mixture of ethanol and ether.

EXAMPLE 10

A mixture of N-(2-oxopropyl)phenylacetamide (28.65 g.) 1-p-benzyloxyphenyl-2-aminoethanol (36.45 g.), Molecular Sieve Type 4A (B.D.H.; 600 g.) and ethanol (450 ml.) is heated under reflux for 24 hours, cooled and filtered and an excess of sodium borohydride (approximately 10.0 g.) is added. The mixture is stirred for 1 hour and then evaporated to dryness, and the residue is shaken with a mixture of water and ethyl acetate. The organic layer is separated, washed with water, dried and evaporated to dryness. The residue is stirred with ether and the ethereal solution decanted off. The residue is dissolved in ethanol and an excess of a solution of oxalic acid in ether is added. The mixture is filtered and the solid residue is dissolved in acetic acid and shaken with hydrogen and a 30 percent palladium-on-charcoal catalyst at atmospheric pressure and laboratory temperature until uptake of hydrogen ceases. The mixture is filtered, the filtrate is evaporated to dryness and the residue is crystallised from a mixture of isopropanol and ether. There is thus obtained 1-p-hydroxyphenyl-2-( 1-methyl-2-phenylacetamidoethyl)aminoethanol oxalate, m.p. 69°–72°C. (with decomposition).

The N-(2-oxopropyl)phenylacetamide used as starting material may be obtained as follows:-

Jones' reagent (2.67N-chromium trioxide in aqueous sulphuric acid; 480 ml.) is added during 45 minutes to a stirred solution of 1-phenylacetamidopropan-2-ol (306.4 g.) in chloroform (1600 ml.) which is maintained at 20°C. The chloroform layer is separated, the aqueous layer is washed with chloroform and the combined chloroform solutions are dried and evaporated to dryness. The residue is stirred with ethyl acetate and the mixture is filtered. There is thus obtained as solid product N-(2-oxopropyl)phenylacetamide, m.p. 126°C.

EXAMPLE 11

Isopropyl isocyanate (0.85 g.) is added to a solution of 1-p-benzyloxyphenyl-2-(N-benzyl-N-$\beta$-aminoethylamino)ethanol (3.76 g.) in toluene (40 ml.) and the mixture is kept at laboratory temperature for 16 hours, heated until all solid has dissolved, diluted with petroleum ether (b.p. 60°–80°C.) and cooled. The mixture is filtered and the solid product is washed with ether and dissolved in acetic acid. The solution is shaken with hydrogen and a 30 percent palladium-on-charcoal catalyst at atmospheric pressure and laboratory temperature until uptake of hydrogen ceases, and is then filtered. The filtrate is evaporated to dryness, the residue is dissolved in ethanol and an excess of a solution of oxalic acid in ether is added. The mixture is filtered and the solid product is crystallised from ethanol. There is thus obtained 1-p-hydroxyphenyl-2-($\beta$-3-isopropylureidoethyl)aminoethanol hydrogen oxalate hemihydrate, m.p. 194°–195°C. (with decomposition).

The 1-p-benzyloxyphenyl-2-(N-benzyl-N-$\beta$-aminoethyl-amino)ethanol used as starting material may be obtained as follows:-

A mixture of 1-p-benzyloxyphenyl-2-($\beta$-isobutyramidoethyl)aminoethanol (88g.; Example 4) and potassium hydroxide (200 g.) in ethanol (400 ml.) is heated under reflux for 96 hours, diluted with water (1500 ml.) and extracted with ether. The extract is washed with water, dried over potassium carbonate and evaporated to dryness. There is thus obtained as oily residue 1-p-benzyloxyphenyl-2-(N-benzyl-N$\beta$-aminoethylamino)ethanol which is used without further purification.

The process described above is repeated except that the appropriate isocyanate is used in place of isopropyl isocyanate. There are thus obtained the compounds described in the following table:-

HO—⟨C₆H₄⟩—CHOH.CH$_2$NH-CH$_2$CH$_2$-NHCONH-R

| R | salt | m.p.°C. | crystallisation solvent |
|---|---|---|---|
| methoxymethyl | oxalate | 60–63(d) | (stir with acetone |
| cyclohexyl | oxalate sesquihydrate | 97–100 | ethanol/ether |
| 4-biphenylyl | oxalate hemihydrate | 128–130 | methanol |
| butoxycarbonylmethyl | oxalate hydrate | 65 | ethanol/ether |
| o-tolyl | hydrogen oxalate hydrate | 146–148(d) | ethanol/ether |

EXAMPLE 12

A mixture of 1-p-benzyloxyphenyl-2-(N-benzyl-N-β-aminoethylamino)ethanol (3.76 g.), phenylacetyl chloride (2.32 g.), anydrous potassium carbonate (2.76 g.) and toluene (40 ml.) is stirred at laboratory temperature for 16 hours and then filtered. The filtrate is washed with water, dried and evaporated to dryness and the residue is dissolved in acetic acid. The solution is shaken with hydrogen and a 30 percent palladium-on-charcoal catalyst until uptake of hydrogen ceases, and is then filtered. The filtrate is evaporated to dryness and the resiue is dissolved in ethanol and treated with an excess of a solution of oxalic acid in ether. The mixture is filtered and the residue is crystallised from ethanol. There is thus obtained 1-p-hydroxyphenyl-2-(β-phenylacetamidoethylamino)ethanol oxalate, m.p. 100°–102°C. (with decomposition).

The process described above is repeated except that the appropriate acid chloride is used in place of phenylacetyl chloride. There are thus obtained the compounds described in the following table;-

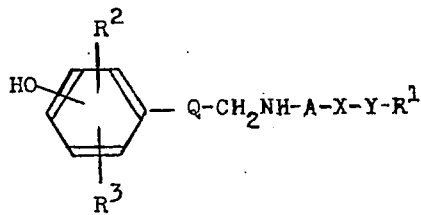

| $R^1$ | salt | m.p.°C. | crystallisation solvent |
|---|---|---|---|
| phenyl | hydrogen oxalate hemihydrate | 218(d) | ethanol/ ether |
| cyclohexyl | hydrogen oxalate hemihydrate | 189–190(d) | ethanol/ ether |
| ethyl* | oxalate | 192 | (stir with ethanol) |

*Propionic anhydride is used instead of propionyl chloride.

What we claim is:

1. A phenylethylamine derivative selected from compounds of the formula:-

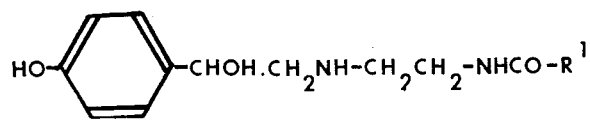

wherein A is alkylene of up to 6 carbon atoms, wherein Q is carbonyl or hydroxymethylene, wherein $R^1$ is alkyl or cycloalkyl each of up to 6 carbon atoms, or aryl of the formula:-

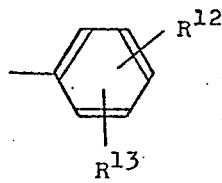

wherein $R^2$, $R^3$, $R^{12}$ and $R^{13}$, which may be the same or different, each is hydrogen, halogen, hydroxy, amino or hydroxymethyl, alkyl, alkoxy, acylamino or alkanesulphonamido each of up to 6 carbon atoms, or aryl of up to 12 carbon atoms, wherein X is NHCO and wherein Y is iminoalkylenecarbonyloxy of up to 6 carbon atoms, or imino, or -NR$^1$- wherein $R^1$ is as stated above: and the acid-addition salts thereof.

2. A phenylethylamine derivative as claimed in claim 1 selected from compounds of the formula given in claim 1 wherein A is ethylene, trimethylene, tetramethylene, hexamethylene or 1-methylethylene, wherein $R^1$ is methyl, ethyl, n-propyl, isopropyl, n-butyl, isobutyl, t-butyl, cyclopropyl, cyclopentyl or cyclohexyl or is aryl of the formula:-

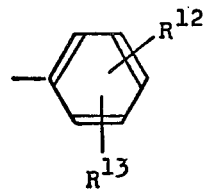

wherein $R^2$, $R^3$, $R^{12}$ and $R^{13}$, which may be the same or different, each is hydrogen, fluorine, chlorine, bromine, iodine, hydroxy, amino, hydroxymethyl, methyl, ethyl, n-propyl, allyl, methoxy, isopropoxy, allyloxy, acetamido, methansulphonamido or phenyl, wherein Y is imino, methylimino, methyleneoxy, or iminomethylenecarbonyloxy, and wherein Q and X are as stated in claim 1; and the acid-addition salts thereof.

3. A phenylethylamine derivative as claimed in claim 1 selected from compounds of the formula given in claim 1 wherein A is ethylene or 1-methylethylene, wherein Q is hydroxymethylene, wherein $R^1$ is alkyl or cycloalkyl each of up to 6 carbon atoms or unsubstituted phenyl, wherein $R^2$ is hydrogen, hydroxy or methyl, wherein $R^3$ is hydrogen, wherein X is -NHCO- and wherein Y is imino; and the acid-addition salts thereof.

4. A phenylethylamine derivative selected from compounds of the formula given in claim 1 wherein the essential hydroxy is in the 4-position of the benzene ring and $R^2$ is hydrogen or hydroxy in the 3-position of the benzene ring; and the acid-addition salts thereof.

5. A compound as claimed in claim 1 selected from 1-p-hydroxyphenyl-2-(β-3-phenylureidoethyl)aminoethanol;
1-p-hydroxyphenyl-2-(β-3-methoxymethylureidoethyl)aminoethanol;
1-p-hydroxyphenyl-2-(β-3-n-butoxycarbonylmethylureidoethyl)aminoethanol;
1-(3,4-dihydroxyphenyl)-2-(β-3-phenylureidoethyl)aminoethanol; and
1-(4-hydroxy-3-hydroxymethylphenyl)-2-(β-3-phenylureidoethyl)-aminoethanol;
and the acid-addition salts thereof.

6. An acid-addition salt as claimed in claim 1 which is a hydrochloride, hydrobromide, phosphate, sulphate, oxalate, lactate, tartrate, fumatrate, acetate, salicylate, citrate, benzoate, β-naphthoate, adipate or 1,1-methylene-bis(2-hydroxy-3-naphthoate), or a salt derived from a sulphonated polystyrene resin.

* * * * *